(12) United States Patent
Ko (10) Patent No.: US 8,022,042 B2
(45) Date of Patent: *Sep. 20, 2011

(54) COMPOSITION AND METHODS FOR THE TREATMENT OF CANCER

(76) Inventor: Young Hee Ko, Owings Mills, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/697,169

(22) Filed: Jan. 29, 2010

(65) Prior Publication Data

US 2010/0197612 A1    Aug. 5, 2010

Related U.S. Application Data (63) Continuation-in-part of application No. 11/706,868, filed on Feb. 14, 2007, now Pat. No. 7,754,693.

(60) Provisional application No. 60/773,653, filed on Feb. 16, 2006, provisional application No. 61/148,385, filed on Jan. 29, 2009.

(51) Int. Cl.
| | |
|---|---|
| A61K 31/70 | (2006.01) |
| A61K 31/715 | (2006.01) |
| A61K 31/415 | (2006.01) |
| A61K 31/19 | (2006.01) |
| A61K 31/12 | (2006.01) |

(52) U.S. Cl. ............... 514/23; 514/53; 514/54; 514/396; 514/557; 514/675

(58) Field of Classification Search ............... 514/23, 514/53, 54, 396, 557, 675

See application file for complete search history.

(56) References Cited

U.S. PATENT DOCUMENTS

| | | | |
|---|---|---|---|
| 4,536,387 A | 8/1985 | Sakamoto et al. | |
| 5,759,547 A | 6/1998 | Maione | |
| 5,759,837 A | 6/1998 | Kuhajda et al. | |
| 5,854,067 A | 12/1998 | Newgard et al. | |
| 6,031,000 A | 2/2000 | Nissen et al. | |
| 6,284,786 B1 | 9/2001 | Casciari et al. | |
| 6,312,662 B1 | 11/2001 | Erion et al. | |
| 6,448,030 B1 | 9/2002 | Rust et al. | |
| 6,670,330 B1 | 12/2003 | Lampidis et al. | |
| 7,338,940 B2 | 3/2008 | Lampidis et al. | |
| 7,754,693 B2 * | 7/2010 | Ko | 514/23 |
| 2001/0046997 A1 | 11/2001 | Abraham et al. | |
| 2002/0006915 A1 | 1/2002 | Mack Strong et al. | |
| 2002/0068711 A1 | 6/2002 | Pedersen et al. | |
| 2003/0018166 A1 | 1/2003 | Sacchettini et al. | |
| 2003/0087961 A1 | 5/2003 | Ko et al. | |
| 2003/0139331 A1 | 7/2003 | Martin et al. | |
| 2004/0029826 A1 | 2/2004 | Sokoloff et al. | |
| 2004/0126789 A1 | 7/2004 | Park et al. | |
| 2004/0167079 A1 | 8/2004 | Tidmarsh | |
| 2004/0167196 A1 | 8/2004 | Tidmarsh | |
| 2006/0058383 A1 | 3/2006 | Huang et al. | |
| 2006/0154867 A1 | 7/2006 | Sokoloff et al. | |
| 2006/0172953 A1 | 8/2006 | Tidmarsh et al. | |

FOREIGN PATENT DOCUMENTS

WO   WO 2008/076964   6/2008

OTHER PUBLICATIONS

Ko et al., Advanced cancers: eradiction in all cases using 3-bromopyruvate therapy to deplete ATP, Biochemical and Biophysical Research Communications, 2004, 324, 269-275.
Kerr et al; Phase I Clinical DNA Pharmacokinetic Study of Leucovorin and Infusional Hepatic Arterial Fluorouracil; Journal of Clinical Oncology; Dec. 1995; vol. 13, No. 12; p. 2968-2972.
Lin et al.; Effects of 90Y-Microsphers on Liver Tumors: Comparison of Intratumoral Injection Method and Inta-Arterial Injection Method; Nov. 2000; The Journal of Nuclear Medicine; vol. 41, No. 11; p. 1892-1897.
Arafat et al.; Toxicities Related to Intraarterial Infusions of Cisplatin and Etoposide in Patients with Brain Tumors; Journal of Neurooncology; 1999; vol. 42 pp. 73-77.
Bar et al.; Sorbitol Removal by the Metastatic Liver: a Predictor of Systemic Toxicity of Intra-Arterial Chemotherapy in Patients with Liver Metastases; 1999; Journal of Hepatology; vol. 30; pp. 1112-1118.
Geshwind et al.; Novel Therapy for Liver Cancer: Direct Intraarterial Injection of a Potent Inhibitor of ATP Production; Jul. 15, 2002; Cancer Research; vol. 62; p. 3909-3913.
Gobin et al.; Intraarterial Chemotherapy for Brain Tumors by Using a Spatial Dose Fractionation Algorithm and Pulsatile Delivery; Mar. 2001; Radiology; vol. 218 No. 3; p. 724-732.
Ko et al.; Glucose Catabolism in the Rabbit VX2 Tumor Model for Liver Cancer: Characterization and Targeting Hexokinase; 2001; Cancer Letters; vol. 173; pp. 83-91.

(Continued)

Primary Examiner — Raymond Henley, III
(74) Attorney, Agent, or Firm — Thorpe North & Western LLP (57) ABSTRACT

The present invention discloses anti-cancer compositions, and associated methods, including an anti-cancer composition comprising: a cellular energy inhibitor having the structure according to formula I

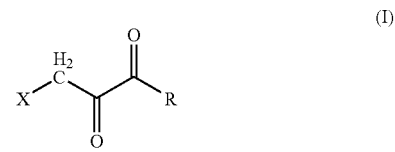

(I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl. The anti-cancer composition can additionally comprise at least one sugar, which stabilizes the cellular energy inhibitor by substantially preventing the inhibitor from hydrolyzing. Also, the anti-cancer composition can comprise a glycolysis inhibitor. Further, the anti-cancer composition can comprise a biological buffer that is present in an amount sufficient to at least partially deacidify the cellular energy inhibitor and neutralize metabolic by-products of the cellular energy inhibitor.

46 Claims, 2 Drawing Sheets

OTHER PUBLICATIONS

Kostron et al.; Photodynamic Treatment of Malignant Brain Tumors; Sep. 28, 1990; Jg 102, Heft 18: 531-535; (Abstract Only).

Mathupala et al.; Glucose Catabolism in Cancer Cells, Identification and Characteriszation of a Marked Activation Response of the Type II Hexokinase Gene to Hypoxic Conditions; Nov. 16, 2001; vol. 276, No. 46; pp. 43407-43412.

Pedersen et al.; Mitochondrial Bound Type II Hexokinase: a Key Player in the Growth and Survival of Many Cancers and an Ideal Prospect for Therapeutic Intervention; Biochimica et Biophysica Acta; 2002; vol. 1555 pp. 14-20.

Soulen et al.; Intraarterial Chemotherapy with Limb-Sparing Resection of Large Soft-Tissue Sarcomas of the Extremities; JFIR; Nov. 1992; vol. 3; 659-663.

Wang et al.; Isolated Lower Extremity Chemotherapeutic Infusion for Treatment of Osteosarcoma: Experimental Study and Preliminary Clinical Report; J. Vasc. Interv. Radiol.; Jun. 2001; vol. 12; pp. 731-737.

Johns Hopkins Medical Institutions Office of Communications and Public Affairs; Energy Blocker may be Potential Liver Cancer Treatment; www.hopkinsmedicine.org/press/2002/July/020715.htm.

Ko et al.; Alkylation of Isocitrate Lyase from *Escherichia coli* by 3-Bromopyruvate; May 1, 1990; Archives of Biochemistry and Biophysics; vol. 278, No. 2; pp. 373-380.

Oya et al.; Evaluation of Experimental Liver Tumors Using Fluorine-18-2-Fluoro-2-Deoxy-D-Glucose PET; J. Nuci. Med.; Dec. 1993; vol. 34, No. 12; pp. 2124-2129.

Arora et al.; Functional Significance of Mitochondrial Bound Hexinase in Tumor Cell Metabolism, Evidence for Preferential Phosphorylation of Glucose by Intramitochondrially Generated ATP; The Journal of Biological Biochemistry; Nov. 25, 1988; vol. 263, No. 33; p. 17422-17428.

Mathupala et al.; Glucose Catabolism in Cancer Cells, Isolation, Sequence, and Activity of the Promoter for Type II Hexokinase; Tthe Journal of Biological Chemistry; Jul. 14,1995; vol. 270, No. 28; pp. 16918-16925.

Rempel et al.; Glucose Catabolism in Cancer Cells: Amplification of the Gene Encoding Type II Hexokinase; Cancer Research; Jun. 1, 1996; vol. 56, pp. 2468-2471.

Parry et al.; Intracellular Localization and Properties of Particulate Hexokinase in the Novikoff Ascites Tumor, Evidence for an Outer Mitochondrial Membrane Location; The Journal of Biological Chemistry; Sep. 25, 1983; vol. 258, No. 18; pp. 10904-10912.

Bustamante et al.; Energy Metabolism of Tumor Cells, Requirement for a Form of Hexokinase with a Propensity for Mitochondrial Binding; The Journal of Biological Chemistry; Aug. 25, 1981; vol. 256, No. 16; pp. 8699-8704.

Weinhouse; Glycolysis, Respiration, and Anomalous Gene Expression in Experimental Hepatomas: G.H.A. Clowes Memorial Lecture; Cancer Research; Oct. 1972; vol. 32, No. 10; pp. 2007-2016.

Sharma et al.; Structure of Isocitrate Lyase, A Persistence Factor of Mycobacterium Tuberculosis; Nature Structural Biology; Aug. 2000; vol. 7 No. 8; pp. 663-668.

Chen et al.; The Warburg Effect and its Cancer Therapeutic Implications; Journal of Bioenergestics and Bioenergestic and Biomembranes; 2007; vol. 39, No. 3; pp. 267-274.

Pelicano et al.; Glycolysis Inhibition for Anticancer Treatment; Oncogene; 2005; vol. 25; pp. 4633-4646.

Ihrlund et al.; 3-Bromopyruvate as Inhibitor of Tumor Cell Energy Metabolism and Chemopotentiator of Platinum Drugs; Molecular Oncology; Jun. 2008; vol. 2, No. 1; p. 94-101.

Kang et al.; 2-Deoxyglucose: An Anticancer and Antiviral Therapeutic, But Not Any More a Low Glucose Mimetic; Life Sciences; Feb. 2006; vol. 78, No. 12; pp. 1392-1399.

PCT Application PCT/US2010/022664; filed Jan. 29, 2010; Young Hee Ko; ISR mailed Oct. 28, 2010.

Pedersen; Tumor Mitoichondria and the Bioenergetics of Cancer Cells; Prog. Exp. Tumor Res.; 1978; vol. 22; p. 190-274.

Fiebig et al.; Relevance of tumor models for Anticancer Drug Development; 1999; Contrib. Oncol. Basel. Karger; vol. 54; pp. 109-120.

Ko et al.; Advanced Cancers: Eradication in all cases using 3-Bromopyruvate Therapy to Deplete ATP; 2004; Biochemical and Biophysical Research Communications; vol. 324; pp. 269-275.

Pederson, P., "Energy Blocker" Kills Big Tumors in Rats; Audio File-Johns Hopkins Medicine, Office of Corporate Communications; Oct. 14, 2004.

Ko et al.; Advanced Cancers: Eradication in All Cases Using 3-Bromopyruvate Therapy to Deplete ATP; Press Release, BBRC Supporting Online Material; Nov. 5, 2004.

\* cited by examiner

COMPOSITION AND METHODS FOR THE TREATMENT OF CANCER

CROSS-REFERENCE TO RELATED APPLICATIONS AND CLAIM OF PRIORITY

This application is a continuation-in-part of U.S. patent application Ser. No. 11/706,868 filed on Feb. 14, 2007, which claims the benefit of Provisional Application Ser. No. 60/773,653, filed Feb. 16, 2006, and the current application also claims the benefit of U.S. provisional patent application Ser. No. 61/148,385 filed on Jan. 29, 2009, all of which are incorporated by reference in their entireties.

BACKGROUND

Each year, hundreds of thousands of men, women, and children in the United States are afflicted with some form of cancer. Worldwide, millions die of cancers including those of the bone, bladder, blood (leukemias), brain, breast, colon, cervix, esophagus, intestine, kidney, liver, lung, mouth, nose, nerves, ovaries, pancreas, prostate, skin, stomach, testis, throat, thyroid, uterus, and vagina.

Over the years, a number of methods have been used to treat cancer including radiation and chemotherapy. The primary goal of these treatments is to kill all the cancer cells. However, many healthy cells are invariably destroyed in a race to kill the cancer cells before the treatment(s) kill the patient. Even today, the more measured and quantitative uses of radiation and chemotherapy can cause illness and even death in some patients. At the same time, in some types of cancer, the malignant cells remain difficult to treat.

Consequently, ongoing research and developmental efforts continue in the medicinal arts involving the treatment of various cancers.

SUMMARY

It has been recognized by the present inventor that it would be advantageous to develop an anti-cancer composition that is effective over an array of cancers, that is safe for use in humans, and that avoids or at least minimizes adverse drug experiences associated with traditional cancer treatments.

Briefly, and in general terms, the invention is directed to an anti-cancer composition comprising: a cellular energy inhibitor having the structure according to formula I (I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl. Additionally, the anti-cancer composition can comprise at least one sugar, which stabilizes the cellular energy inhibitor by substantially preventing the inhibitor from hydrolyzing. The anti-cancer composition can further comprise a glycolysis inhibitor. Further, the anti-cancer composition can also comprise a biological buffer that is present in an amount sufficient to at least partially deacidify the cellular energy inhibitor and neutralize metabolic by-products of the cellular energy inhibitor.

In one embodiment, a method for the treatment of cancer can comprise administering to a subject any of the anti-cancer compositions described herein in a therapeutically effective amount.

In another embodiment, a method of minimizing toxicity of a cellular energy inhibitor of formula (I) to a subject receiving the cellular energy inhibitor can comprise combining in the subject, the cellular energy inhibitor with a biological buffer that is present in an amount sufficient to at least partially deacidify the cellular energy inhibitor and neutralize metabolic by-products of the cellular energy inhibitor due to its chemical reaction and/or cellular metabolism.

In yet another embodiment, a method of minimizing an adverse drug experience associated with administration of any of the anti-cancer compositions as described herein to a subject can comprise administering the anti-cancer composition to the subject at a time when the subject's blood insulin/glucagon ratio is in the range of about 1 to about 10.

In still another embodiment, a method for assessing killing efficacy of any of the anti-cancer compositions described herein in a subject can comprise measuring a lactic acid level in the subject prior to administration of the anti-cancer composition; administering the anti-cancer composition to the subject; measuring the lactic acid level in the subject after administration of the anti-cancer composition; and determining the killing efficacy by measuring and/or correlating the difference between the lactic acid levels as a function of treatment time.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIGS. 4(*a*) and 4(*b*) show a series of photographs of lungs having metastatic tumors without treatment and with treatment using 3-bromopyruvate, respectively, in accordance with an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Before the present invention is disclosed and described, it is to be understood that this disclosure is not limited to the particular process steps and materials disclosed herein because such process steps and materials may vary somewhat. It is also to be understood that the terminology used herein is used for the purpose of describing particular embodiments only. The terms are not intended to be limiting because the scope of the present disclosure is intended to be limited only by the appended claims and equivalents thereof.

It must be noted that, as used in this specification and the appended claims, the singular forms "a," "an," and "the" include plural referents unless the context clearly dictates otherwise.

The composition of the present invention may include a pharmaceutically acceptable carrier, and other ingredients as dictated by the particular needs of the specific dosage formulation. Such ingredients are well known to those skilled in the art. See for example, Gennaro, A. *Remington: The Science and Practice of Pharmacy* 19$^{th}$ ed. (1995), which is incorporated by reference in its entirety.

As used herein, "administration," and "administering" refer to the manner in which a drug is presented to a subject. Administration can be accomplished by various art-known routes such as oral, alimentary, parenteral, transdermal, inhalation, implantation, etc. Thus, an oral administration can be achieved by drinking, swallowing, chewing, sucking of an oral dosage form comprising the drug. Parenteral administration can be achieved by injecting a drug composition intravenously, intra-arterially, intramuscularly, intrathecally, or subcutaneously, etc. Transdermal administration can be accomplished by applying, pasting, rolling, attaching, pouring, pressing, rubbing, etc., of a transdermal preparation onto a skin surface. These and additional methods of administration are well-known in the art.

As used herein, "non-oral administration" represents any method of administration in which a drug composition is not provided in a solid or liquid oral dosage form, wherein such solid or liquid oral dosage form is traditionally intended to substantially release and or deliver the drug in the gastrointestinal tract beyond the mouth and/or buccal cavity. Such solid dosage forms include conventional tablets, capsules, caplets, etc., which do not substantially release the drug in the mouth or in the oral cavity.

It is appreciated that many oral liquid dosage forms such as solutions, suspensions, emulsions, etc., and some oral solid dosage forms may release some of the drug in the mouth or in the oral cavity during the swallowing of these formulations. However, due to their very short transit time through the mouth and the oral cavities, the release of drug from these formulations in the mouth or the oral cavity is considered de minimus or insubstantial, unless otherwise indicated. Thus, buccal patches, adhesive films, sublingual tablets, and lozenges that are designed to release the drug in the mouth are non-oral compositions for the present purposes.

In addition, it is understood that the term "non-oral" includes parenteral, transdermal, inhalation, implant, and vaginal or rectal formulations and administrations. Further, implant formulations are to be included in the term "non-oral," regardless of the physical location of implantation. Particularly, implantation formulations are known which are specifically designed for implantation and retention in the gastrointestinal tract. Such implants are also considered to be non-oral delivery formulations, and therefore are encompassed by the term "non-oral."

As used herein, "subject" refers to a mammal that may benefit from the administration of a drug composition or method of this invention. Examples of subjects include humans, and other animals such as horses, pigs, cattle, sheep, goats, dogs (felines), cats (canines), rabbits, rodents, primates, and aquatic mammals. In one embodiment, subject can refer to a human.

As used herein, "effective amount" or "therapeutically effective amount," or similar terms, refers to a non-toxic but sufficient amount of a drug, to achieve therapeutic results in treating a condition for which the drug is known to be effective or has been found to be effective as disclosed herein. Various biological factors may affect the ability of a delivered substance to perform its intended task or the amount of drug needed to provide a therapeutic result. Therefore, an "effective amount" or "therapeutically effective amount" may be dependent on such biological factors. The determination of an effective amount or therapeutically effective amount is well-within the ordinary skill in the art of pharmaceutical and medical sciences based on known techniques in the art as well as the present disclosure. See for example, Curtis L. Meinert & Susan Tonascia, *Clinical Trials: Design, Conduct, and Analysis*, Monographs in Epidemiology and Biostatistics, vol. 8 (1986).

As used herein, "drug," "active agent," "bioactive agent," "pharmaceutically active agent," "therapeutically active agent" and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category, it is understood that such recitation is intended to include the active agent per se, as well as pharmaceutically acceptable salts, or compounds significantly related thereto, including without limitation, prodrugs, active metabolites, isomers, and the like.

As used herein, "cellular energy inhibitor" refers to a compound that inhibits glycolysis and mitochondria function of a cancer cell.

As used herein, "glycolysis inhibitor" refers to a compound that inhibits, reduces, or stops, glycolysis in a cancer cell.

As used herein, "mitochondria inhibitor" refers to a compound that inhibits, reduces, or stops mitochondria function in a cancer cell.

As used herein, the terms "dosage form", "formulation" and "composition" are used interchangeably and refer to a mixture of two or more compounds, elements, or molecules. In some aspects the terms "dosage form", "formulation" and "composition" may be used to refer to a mixture of one or more active agents with a carrier or other excipients.

As used herein, "carrier" or "pharmaceutically acceptable carrier" refers to a substance with which a drug may be combined to achieve a specific dosage formulation for delivery to a subject. In the some aspects of the present invention, the carriers used may or may not enhance drug delivery. As a general principle, carriers do not react with the drug in a manner which substantially degrades or otherwise adversely affects the drug, except that carriers may react with a drug to prevent it from exerting a therapeutic effect until the drug is released from the carrier. Further, the carrier, or at least a portion thereof must be suitable for administration into a subject along with the drug.

As used herein, the terms "release", "release rate" 'dissolution" "dissolution rate", are used interchangeably to refer to the discharge or liberation of a substance, including without limitation a drug, from the dosage form into a surrounding environment such as an aqueous medium either in vitro or in vivo.

As used herein, "controlled release," "sustained release," "modified release," "delayed release", "extended release" and "non-immediate release" are used interchangeably and refer to release of active agent or agents from a dosage form into the target environment or medium over a period of time that is at least 5% slower than the equivalent dosage containing immediate release (IR) formulations. In one embodiment, the "controlled release," "sustained release," "modified release" delayed release" "extended release" or non-immediate release" systems or compositions can provide for a release of the active agent or agents from the dosage form into the target environment or medium over a period of time that is at least 10 wt % slower than the equivalent dosage form containing immediate release (IR) formulations.

As used herein, "release modifying agent", "release modulating agent", and "release modifiers" are used interchangeably and refer to pharmaceutically acceptable agents or devices that are capable to alter, increase or decrease, or otherwise customize, the release rates of at least one of the contents of the compositions or dosage forms thereof, when exposed to an aqueous use environment.

As used herein, "admixed" means that at least two components of the composition can be partially or fully mixed, dispersed, suspended, dissolved, or emulsified in one another. In some cases, at least a portion of the drug may be admixed in at least one carrier substance.

As used herein, "adverse drug experience" refers to any adverse event associated with the use of a drug in a subject, including the following: an adverse event occurring in the course of the use of a drug product in professional practice; an adverse event occurring from drug overdose whether accidental or intentional; an adverse event occurring from drug abuse; an adverse event occurring from drug withdrawal; and any failure of expected pharmacological action. The adverse drug experience may lead to a substantial disruption of a person's ability to conduct normal life functions. In some instances, the adverse drug experience may be serious or life threatening.

While some of the adverse drug experiences may be expected, in some instances, such experiences may be unexpected. "Unexpected," refers to an adverse drug experience that has not been previously catalogued by a responsible governmental agency (such as the Food and Drug Administration of the United States) and or not provided in the current labeling for the drug product.

The unexpected adverse experiences may include events that may be symptomatically and pathophysiologically related to a known event, but differ from the event because of greater severity or specificity. For example, under this definition, hepatic necrosis would be unexpected (by virtue of greater severity) if the known event is elevated hepatic enzymes or hepatitis. Similarly, cerebral thromboembolism and cerebral vasculitis would be unexpected (by virtue of greater specificity) if the known event is cerebral vascular accidents. For a more comprehensive definition and description of adverse drug experience, see 21 C.F.R. §314.80, which is incorporated by reference in its entirety.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still contain such an item as long as there is no measurable effect thereof. Unless otherwise, indicated "substantially" preventing hydrolysis or hydrolyzing refers to the ability of sugar(s) to stabilize the cellular energy inhibitor for at least one hour while such that at least 50% of the cellular energy inhibitor does not hydrolyze.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3.5, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

For example, a concentration range of 0.5 to 15 mM should be interpreted to include not only the explicitly recited concentration limits of 0.5 mM and 15 mM, but also to include individual concentrations within that range, such as 0.5 mM, 0.7 mM, 1.0 mM, 5.2 mM, 11.6 mM, 14.2 mM, and sub-ranges such as 0.5-2.5 mM, 4.8-7.2 mM, 6-14.9 mM, etc. This interpretation should apply regardless of the breadth of the range or the characteristic being described.

It has been recognized by the present inventor that an alternative to tradition anti-cancer compositions and treatments can be achieved by targeting the energy production of a cancer cell. Without intending to be bound by any particular theory, the present inventor has found that certain cellular energy inhibitors can be used to treat cancers. Generally, there are two energy (ATP) production factories inside the cell, i.e., glycolysis and oxidative phosphorylation by mitochondria. In normal cells, about 5% of the total cellular energy (ATP)

production is derived from glycolysis and about 95% from the mitochondria. In cancer cells, the energy production by glycolysis can be significantly increased (up to 60%). This dramatic increase in glycolysis in cancer cells results in a significant increase in lactic acid production.

Most cancers (>90%) exhibit this common metabolic phenotype. This is called the "Warburg Effect", i.e., significant increase in glycolysis in cancer cells even in the presence of oxygen. The most frequent cancer detection method used clinically, i.e., Positron Emission Tomography (PET) is based on this metabolic phenotype, i.e., the "Warburg effect". Cancer cells that exhibit the "Warburg effect" pump out the produced lactic acid via a transporter (i.e., monocarboxylate transport isoforms). The number of these transporters (considered as doors or gates) in cancer cells is much greater than in normal cells.

Figure 1:
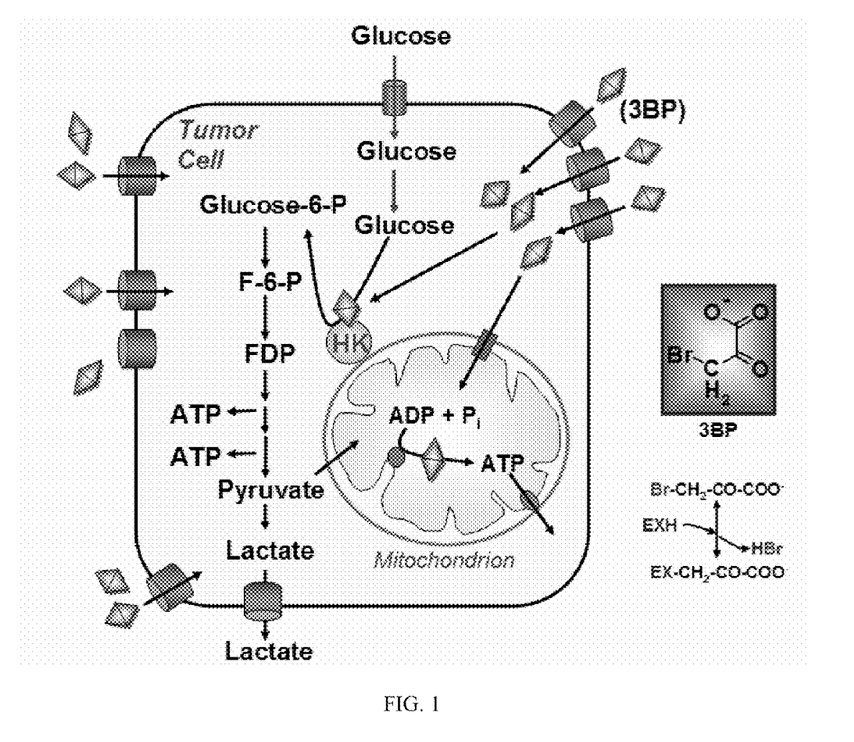
FIG. 1 is a schematic of a cancer cell energy production in accordance with an embodiment of the present invention.
Figure 2:
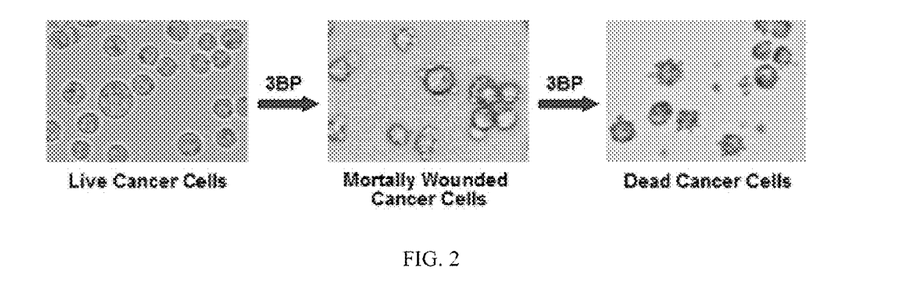
FIG. 2 is a series of photographs of cancer cells treated with 3-bromopyruvate in accordance with an embodiment of the present invention.

The presently disclosed cellular energy inhibitors, shown as 3-bromopyruvate (3BP) (a lactic acid analog) in FIG. 1, are small chemicals and can mimic the lactic acid chemical structure; depicted as a small diamond in FIG. 1. Therefore, cellular energy inhibitors disguised as lactic acid can "trick" the cancer cells and enter like a Trojan horse (FIG. 1). The inhibitors have little effect on normal cells as these contain very few lactic acid transporters. Because of the present cellular energy inhibitors' highly reactive nature, it can destroy the two energy production factories (FIG. 1; one diamond above the hexokinase (HK), shown as 3BP is destroying one energy production factory, i.e., glycolysis, and another red diamond inside the mitochondrion means that 3BP is destroying also this energy production factory). As a result, the cellular energy (ATP) can be depleted very rapidly by cellular energy inhibitors; 3BP in FIG. 1, attack the two factories at the same time causing the cancer cells to rapidly explode (cell membrane rupturing). An example of this can be seen in FIG. 2, which shows liver cancer cells treated with 3BP. Here, the healthy cancer cells are round and iridescent (left picture). However, when they are treated with 3BP, the cell membranes rupture (middle picture) and then die (see cell debris in the far right picture).

In accordance with this, the present disclosure allows for safe administration and use of the present anti-cancer compositions that comprise a cellular energy inhibitor having the structure according to formula I (I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl. Additionally, the anti-cancer composition can comprise at least one sugar, which stabilizes the cellular energy inhibitor by substantially preventing the inhibitor from hydrolyzing. The anti-cancer composition can further comprise a glycolysis inhibitor. Further, the anti-cancer composition can also comprise a biological buffer that is present in an amount sufficient to at least partially deacidify the cellular energy inhibitor and neutralize metabolic by-products of the cellular energy inhibitor.

The present inventor has recognized the need to provide safe and efficacious compositions that allow for treatment of cancers. As previously discussed, the present cellular energy inhibitors can be stabilized by the use of at least one sugar such that the sugar substantially prevents hydrolysis of the cellular energy inhibitor. In this way, the sugar can stabilize the cellular energy inhibitor for at least 1 hour such that at least 50% of the inhibitor does not hydrolyze. In another embodiment, the at least one sugar can stabilize the cellular energy inhibitor for at least 1 hour and prevent at least 95% of the inhibitor from hydrolyzing. In yet another embodiment, the at least one sugar can stabilize the cellular energy inhibitor for at least 2 hours such that at least 95% of the inhibitor does not hydrolyze.

The anti-cancer compositions disclosed herein generally include a compound as described by formula (I). In one embodiment, R of formula (I) can be OH and X of formula (I) can be selected from the group consisting of: a nitro, an imidazole, a halide, a sulfonate, a carboxylate, an alkoxide, and an amine oxide. Additionally, X can be a halide selected from the group consisting of: fluoride, bromide, chloride, and iodide. In one embodiment, X can be a sulfonate selected from the group consisting of: triflate, mesylate and tosylate. In another embodiment, X can be amine oxide. In still another embodiment, the amine oxide can be dimethylamine oxide.

In one embodiment, the cellular energy inhibitor can be a 3-halopyruvate and can be selected from the group consisting of: 3-fluoropyruvate, 3-chloropyruvate, 3-bromopyruvate, 3-iodopyruvate, and combinations thereof. The anti-cancer composition can comprise the cellular energy inhibitor in a concentration from about 0.1 mM to about 25.0 mM. In one embodiment, the anti-cancer composition can comprise the cellular energy inhibitor in a concentration from about 1.0 mM to about 10.0 mM.

While the anti-cancer composition generally comprises at least one sugar, in one embodiment, the anti-cancer composition can comprise other sugars, such as a second sugar. In another embodiment, the anti-cancer composition can comprise a third sugar. At least one of the sugars can be a five-carbon sugar. In one embodiment, at least two of the sugars can be five-carbon sugars. The five-carbon sugars can be independently selected from the group consisting of mannitol, erytritol, isomalt, lactitol, maltitol, sorbitol, xyolitol, dulcitol, ribitol, inositol, sorbitol, and combinations thereof. In one embodiment, at least one of the sugars can be glycerol. In another embodiment, the sugars can be glycerol, inositol, and sorbitol. The anti-cancer composition can comprise glycerol in a range from about 0.1 wt % to about 3 wt %, inositol in a range from about 1 wt % to about 5 wt %, and sorbitol in a range from about 30 wt % to about 50 wt %. Additionally, each of the sugars may be added in a volume up to a maximum solubility of the sugar in the formulation or composition.

In one embodiment, the anti-cancer composition can comprise the at least one sugar in a concentration from about 0.1 mM to about 250 mM. In another embodiment, the anti-cancer composition can comprise the at least one sugar in a concentration from about 0.5 mM to about 25 mM.

Generally, the anti-cancer composition can comprise a glycolysis inhibitor. In one embodiment, the glycolysis inhibitor can be 2-deoxglucose. The anti-cancer composition can comprise the glycolysis inhibitor in a concentration from about 0.1 mM to about 25.0 mM. In one embodiment, the anti-cancer composition can comprise the glycolysis inhibitor in a concentration from about 1 mM to about 5 mM.

Generally, the anti-cancer composition can include a biological buffer that is present in an amount sufficient to at least partially deacidify the cellular energy inhibitor and neutralize metabolic by-products of the cellular energy inhibitor. In one embodiment, the biological buffer can be selected from the group consisting of a citrate buffer, a phosphate buffer, and an acetate buffer. In another embodiment, the biological buffer can be a citrate buffer. In still another embodiment, the biological buffer can be sodium citrate.

As discussed herein, the cellular energy inhibitor is delivered to a cancer cell and is taken up by the cell. After metabolism of the cellular energy inhibitor, the cellular energy inhibitor can cause by-products. In one embodiment, the by-product can be a hydrogen halide. Additionally, the hydrogen halide can be hydrogen bromide or hydrogen iodide. In one embodiment, the hydrogen halide can be hydrogen bromide.

The anti-cancer composition can comprise the biological buffer in a concentration of from about 0.1 mM to about 200 mM. In one embodiment, the anti-cancer composition can comprise the biological buffer in a concentration of from about 1 mM to about 20 mM. Additionally, the biological buffer can maintain a physiological pH of 4.0 to 8.5. In one embodiment, the biological buffer can maintain a physiological pH of 5.5 to 8.0. In another embodiment, the biological buffer can maintain a physiological pH of 6.8 to 7.8. In still another embodiment, the biological buffer can maintain a physiological pH of 7.3 to 7.6.

In addition to the above components, the anti-cancer compositions described herein can further comprise a halo monocarboxylate compound that is separate from the cellular energy inhibitor. In the cases where the halo monocarboxylate compound can function to inhibit glycolysis and mitochondria function, the halo monocarboxylate can be considered a second cellular energy inhibitor. In one embodiment, the halo monocarboxylate compound can be a halo two-carbon monocarboxylate compound. The halo two-carbon monocarboxylate compound can be selected from the group consisting of 2-fluoroacetate, 2-chloroacetate, 2-bromoacetate, 2-iodoacetate, and mixtures thereof. In one embodiment, the halo two-carbon monocarboxylate compound can be 2-bromoacetate. The anti-cancer composition can comprise the halo two-carbon monocarboxylate compound in a concentration from about 0.01 mM to about 5.0 mM. In one embodiment, the anti-cancer composition can comprise the halo two-carbon monocarboxylate compound in a concentration from about 0.1 mM to about 0.5 mM.

Additionally, the halo monocarboxylate compound can be a halo three-carbon monocarboxylate compound. In one embodiment, the halo three-carbon monocarboxylate compound can be selected from the group consisting of 3-fluorolactate, 3-chlorolactate, 3-bromolactate, 3-iodolactate, and mixtures thereof. The anti-cancer composition can comprise the halo three-carbon monocarboxylate compound in a concentration from about 0.5 mM to about 250 mM. In one embodiment, the anti-cancer composition can comprise the halo three-carbon monocarboxylate compound in a concentration from about 10 mM to about 50 mM.

The anti-cancer compositions described herein can further comprise an antifungal agent and/or antibacterial agent. In one embodiment, the anti-cancer composition can individually comprise the antifungal agent and/or antibacterial agent in a concentration from about 0.01 mM to about 5.0 mM. In another embodiment, the anti-cancer composition can individually comprise the antifungal agent and/or antibacterial agent in a concentration from about 0.05 mM to about 0.5 mM.

The anti-cancer compositions described herein can further comprise a mitochondrial inhibitor in addition to the cellular energy inhibitor. The mitochondrial inhibitor can be selected from the group consisting of: oligomycin, efrapeptin, aurovertin, and mixtures thereof. In one embodiment, the anti-cancer composition can comprise the mitochondrial inhibitor in a concentration from about 0.001 mM to about 5.0 mM. In another embodiment, the anti-cancer composition can comprise the mitochondrial inhibitor in a concentration from about 0.01 mM to about 0.5 mM.

In addition to the above concentrations, the anti-cancer compositions can have various ratios of the components described herein. In one embodiment, the cellular energy inhibitor and biological buffer can be present in a ratio ranging from 1:1 to 1:5 by mM. In another embodiment, the cellular energy inhibitor and glycolysis inhibitor can be present in a ratio ranging from 5:1 to 1:1 by mM. In still another embodiment, the cellular energy inhibitor and the at least one sugar are present in a ratio ranging from 1:1 to 1:5 by mM. In yet another embodiment, the cellular energy inhibitor and the halo two-carbon monocarboxylate compound can be present in a ratio ranging from 20:1 to 4:1 by mM. In still yet another embodiment, the cellular energy inhibitor to mitochondrial inhibitor can be present in a ratio ranging from 20:1 to 40:1 by mM.

As described above, the present anti-cancer compositions can comprise antifungal agents, antibiotics, glycolysis inhibitors, inhibitors of mitochondria, sugars, and biological buffers. Examples of such agents include, but are not limited to, amphotericin B, Efrapeptin, doxorubicin, 2-deoxyglucose (2DOG), analogs of 2DOG, dichloracetic acid (or salt form of dichloroacetate), oligomycin, analogs of oligomycin, glycerol, inositol, sorbitol, glycol, erythritol, threitol, arabitol, xylitol, ribitol, mannitol, dulcitol, iditol, isomalt, maltitol, lactitol, polyglycitol, sodium phosphate, sodium citrate, sodium acetate, sodium carbonate, sodium bicarbonate, sodium pyruvate, sodium lactate, oxaloacetate, isocitrate, aconitate, succinate, fumarate, malate, diluted saline solutions with varying concentrations of NaCl, and water. In addition to the sodium ion that accompanies these biological buffers, calcium and potassium cations can also accompany the biological buffers. The active agents of the anti-cancer composition can include the cellular energy inhibitor, the glycolysis inhibitor, the mitochondria inhibitor, the halo monocarboxylate compound, the antifungal agent, and the antibiotic agent.

In addition to the active agent(s), the composition can also include a pharmaceutically acceptable carrier. The carrier can be a single composition, or a mixture of compositions. Additionally, the carrier can take the form of an encapsulation coat, an absorbing agent, a coating substance, a controlled release device, a release modifying agent, surfactants, or a combination thereof. In some aspects, the carrier can comprise about 1 wt % to about 99 wt % of the total composition. In one embodiment, the carrier can comprise about 5 wt % to about 95 wt % of the total formulation. In another embodiment, the carrier can comprise about 20 wt % to about 80 wt %. In yet a further embodiment, the carrier can comprise about 30 wt % to about 60 wt %. In one embodiment, the carrier can be admixed with the active agent(s). In another embodiment, the carrier can adsorb, entrap, or encapsulate at least a portion of the active agent(s).

Non-limiting examples of compounds that can be used as at least a part of the carrier include without limitation: cetyl alcohol and its esters; stearic acid and its glycerol esters, polyoxyethylene alkyl ethers; polyethylene glycol; polyglycolyzed glycerides; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; proteins; polyoxyethylene glycerides; polyoxyethylene sterols, derivatives, and analogues thereof; polyoxyethylene hydrogenated vegetable oils; reaction mixtures of polyols with at least one member of the group consisting of fatty acids, glycerides, vegetable oils, hydrogenated vegetable oils, and sterols; tocopherol derivatives, sugar esters; sugar ethers; sucroglycerides; waxes, shellac, pharmaceutically acceptable salts thereof, and mixtures thereof.

Non-limiting examples of release modifying agents include without limitation: polyethylene glycols having a weight average molecular weight of about 1000 and more, carbomer, methyl methacrylate copolymers, methacrylate copolyers, hydroxypropyl methyl cellulose, hydroxypropyl cellulose, cellulose acetate phthalate, ethyl cellulose, methyl cellulose and their derivatives; ion-exchange resin; mono-, di-, tri-esters of fatty acids with glycerol; tocopherol and its esters; sucrose esters with fatty acids; polyvinyl pyrollidone; xanthan gums; cetyl alcohol; waxes; fats and oils, proteins, alginate, polyvinyl polymers, gelatins, organic acids, and their derivatives and combinations thereof.

In one embodiment, the carrier can include at least one of celluloses; carbomers; methacrylates; dextrins; gums; inorganic carbonates or salts of calcium or magnesium or both; fatty acid esters; gelatin; lactoses; maltoses; mono-, di- or triglycerides; oils; polyethylene glycols; polyethylene oxide co-polymers; proteins; resins; shellac; silicates; starches; sugar stearates; partially or fully hydrogenated vegetable oils; waxes; and combinations thereof.

In yet another embodiment, the carrier can include at least one of celluloses; carbomers; methacrylates; inorganic carbonates or salts of calcium; inorganic carbonates or salts of magnesium; fatty acids; fatty acid esters; gelatin; lactoses; polyethylene glycol; polyethylene oxide co-polymers; silicates; partially or fully hydrogenated vegetable oils, and combinations thereof.

In yet a further embodiment, the carrier can include at least one of microcrystalline cellulose; hydroxypropyl methylcellulose; ethyl cellulose; silicon dioxide; magnesium aluminosilicate; lactose; xanthan gum; stearic acid; glyceryl distearate; hydrogenated vegetable oil; and combinations thereof.

The formulation, including any dosage form, can include other components or additives. Such additional components and additives are optional. In one aspect, the additive can be a solid at room temperature and have a melting point or range that is greater than about 40° C. Non-limiting examples of additives that can be included in the systems of the present invention include without limitation: fillers such as lactoses, starches, sugars, celluloses, calcium salts, silicon oxides, metallosilicates and the like; disintegrants such as starch glycolate, lauryl sulfate, pregaltinized starch, croscarmellose, crospovidone and the like; binders such as pyrrolidones, methacrylates, vinyl acetates, gums, acacia; tragacanth; kaolins; carrageenan alginates, gelatins and the like; cosolvents such as alcohols, polyethylene glycols having average molecular weight of less than 1000, propylene glycols and the like; surface tension modifiers such as hydrophilic or amphiphlic surfactants; taste-masking agents; sweeteners; microencapsulating agents; process aids such as lubricants, glidants, talc, stearates, lecithin and the like; polymeric coating agents; plasticizers; buffers; organic acids; antioxidants; flavors; colors; alkalizers; humectants; sorbitols; mannitols; osmotic salts; proteins; resins; moisture repelling agents; hygroscopic agents; desiccants; and combinations thereof.

The formulations of the present invention can be formulated into a variety of oral dosage forms including; but not limited to two piece hard gelatin capsules, soft gelatin capsules, beads, beadlets, granules, spherules, pellets, microcapsules, microspheres, nanospheres, nanocapsules, tablets, or combinations thereof. Other forms known to those of ordinary skill in the art may also be used. In one aspect, the oral dosage form may be a capsule or tablet. In another embodiment the oral dosage form may include a multi-component dosage form such as beads in a capsule, a capsule or capsules within a capsule, a tablet or tablets in a capsule, or a multi-layer tablet. It is noteworthy that, when the formulation includes multiple dosage forms, such dosage forms need not be the same. Further, such dosage forms may not be physically present together.

The dosage form, e.g. tablet, may be coated or enrobed with a hydrophilic or a hydrophobic coat material known in the art. In one embodiment, the coat can be a film coat, sugar coat, enteric coat, semipermeable coat, sustained release coat, delayed release coat, osmotic coat and the like. In a further embodiment, the coating material can be a cellulose, gelatin, methacrylate, polyvinyl acetate, povidone, polyethylene glycol, polyethylene oxide, poloxamers, carbomers, shellac, phthalate and the like and their derivatives and combinations thereof. In another embodiment, the coat is a dry powder coat. In one embodiment, the tablet can be a matrix tablet. It is noteworthy that, when present, the coat can be considered as part, or all, of the carrier component of the formulation.

IV

In addition to the compositions described herein, a method for the treatment of cancer, can comprise administering to a subject the anti-cancer compositions as described herein in a therapeutically effective amount. The anti-cancer composition can be administered to the subject when the subject's blood insulin/glucagon ratio is in the range of about 1 to about 10. Additionally, the anti-cancer composition can be administered to the subject after fasting for at least 4 hours. In one embodiment, the anti-cancer composition can be administered to the subject after fasting for 6 hours, and in another embodiment, after fasting for 8 hours. Additionally, the anti-cancer composition can be administered to the subject after fasting for 2 hours. It is noted that such times are not intended to be limiting, and that in one embodiment, the amount of time fasting can be such that the subject's blood insulin/glucagon ratio is in the range of about 2 to about 5.

In addition, the method of administration can be selected from the group consisting of: inter-arterially, intravenously, inter-peritoneally, inhalation, intra-tumorally, orally, topically, and subcutaneously. In one embodiment, the administration can be inter-arterially. The anti-cancer compositions can also be delivered by use of a feeding tube. Intra-tumorally delivery methods can include technologies involving a bronchoscope, an endoscope, and/or a colonoscopy, suppository to any openings, eye drops, nose drops, and ear drops. Additionally, if intra-tumorally injection is going to be performed directly to/in the tumor, ultrasound imaging (or other imaging methods) can be used to aid this injection. Further, intravenous delivery can be combined with a hemodialysis apparatus (i.e. kidney dialysis equipment) to destroy the metastatic circulating cancer cells outside of the blood vessels. In addition, both intravenous and inter-peritoneal can be assisted by utilization of a port system. Furthermore, the present anti-cancer composition can be immediate release, controlled release, or time controlled release. For time controlled release, the present compositions can delivered by implanting wafers, diamond chips, and other implantable devices near or on the tumor site.

Generally, when the anti-cancer composition is administered intra-arterially or intravenously, the administration can be for a duration from about 30 minutes to about 8 hours. In one embodiment, the anti-cancer composition can be intra-arterially or intravenously administered for a duration from about 3 hours to about 5 hours. Additionally, the administration of the anti-cancer composition can be part of a dosing regimen. In one embodiment, the administration can include a regimen lasting from about 1 week to 24 weeks. In another embodiment, the regimen can last from about 4 weeks to 8 weeks.

Generally, the present anti-cancer composition is administered in a therapeutically effective amount as defined herein. In one embodiment, the therapeutically effective amount can include a dosage of, or equivalent to, about 1 mM to about 10 mM of the anti-cancer composition in a volume of 25 ml to 1000 ml.

The anti-cancer compositions described herein can be used to treat any cancer having increased glycolysis; the metabolic phenotype referred to as the "Warburg Effect", as described above. In another embodiment, the anti-cancer compositions can be used to treat any cancer that can be detected by Positron Emission Tomography (PET), which detects this metabolic phenotype. Human cancer cell lines that the present anti-cancer composition has shown to be effective against include liver, cervical, ovarian, lung, breast, colon, neuroblastoma, medulloblastoma, prostate, skin, pancreatic, childhood fibrolamellar hepatocellular carcinoma (FHCC), hepatocellular carcinoma (HCC), non small cell lung cancer. As such, the present cancers that can be treated with the present anti-cancer compositions can be selected from the group consisting of liver, cervical, ovarian, lung, breast, colon, neuroblastoma, medulloblastoma, prostate, skin, pancreatic, childhood fibrolamellar hepatocellular carcinoma (FHCC), hepatocellular carcinoma (HCC), non small cell lung cancer. The present anti-cancer compositions have been used to treat human cancer patients having childhood fibrolamellar hepatocellular carcinoma (FHCC), hepatocellular carcinoma (HCC), non small cell lung cancer, colon cancer, breast cancer, and pancreatic cancer. As such, cancers that can be treated with the present anti-cancer compositions can be selected from the group consisting of childhood fibrolamellar hepatocellular carcinoma (FHCC), hepatocellular carcinoma (HCC), non small cell lung cancer, colon cancer, breast cancer, pancreatic cancer, and combinations thereof.

In one embodiment, the anti-cancer composition can be used to treat liver cancer. In another embodiment, the anti-cancer composition can be used to treat cervical cancer. In still another embodiment, the anti-cancer composition can be used to treat ovarian cancer. In still another embodiment, the anti-cancer composition can be used to treat lung cancer. In still another embodiment, the anti-cancer composition can be used to treat breast cancer. In still another embodiment, the anti-cancer composition can be used to treat colon cancer. In still another embodiment, the anti-cancer composition can be used to treat neuroblastoma. In still another embodiment, the anti-cancer composition can be used to treat medulloblastoma. In still another embodiment, the anti-cancer composition can be used to treat prostate cancer. In still another embodiment, the anti-cancer composition can be used to treat skin cancer. In still another embodiment, the anti-cancer composition can be used to treat breast cancer. In still another embodiment, the anti-cancer composition can be used to treat pancreatic cancer. In still another embodiment, the anti-cancer composition can be used to treat childhood fibrolamellar hepatocellular carcinoma (FHCC). In still another embodiment, the anti-cancer composition can be used to treat hepatocellular carcinoma (HCC). In still another embodiment, the anti-cancer composition can be used to treat small cell and non small cell lung cancer. In still other embodiments the anti-cancer composition can be used to treat vaginal, anal, testicular, nasal, throat, mouth, esophageal, and brain cancers.

In addition to the above treatment of cancer, the present invention provides a method of minimizing toxicity of a cellular energy inhibitor of formula (I) to a subject receiving the cellular energy inhibitor comprising, combining in the subject, the cellular energy inhibitor with a biological buffer that is present in an amount sufficient to at least partially deacidify the cellular energy inhibitor and neutralize metabolic by-products of the cellular energy inhibitor due to its chemical reaction and/or cellular metabolism:

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl. In one embodiment, the cellular energy inhibitor and the biological buffer can be combined prior to administration to the subject.

Additionally, a method of minimizing an adverse drug experience associated with administration of an anti-cancer composition to a subject can comprise administering the anti-cancer composition to the subject at a time when the subject's blood insulin/glucagon ratio is in a range of about 1 to about 10, measured in picomolar (pM). The anti-cancer composition can be any anti-cancer composition described herein. In one embodiment, the insulin/glucagon ratio can be in a range of about 2 to about 5. Without intending to be bound by any particular theory, by administering the present anti-cancer compositions at a time where the subject's blood sugar is low, or the blood insulin/glucagon ratio is low, the normal cells can be protected against any incidental uptake of the anti-cancer active agents. Specifically, such administration can protect the hexokinase 2 (HK-2) enzyme that is present in normal tissues in small amounts. Under low blood sugar conditions, the HK-2 enzyme tends to enter the nucleus of normal cells rather than the cytosolic compartment. The nuclear location of HK-2 provides additional protection against chemo-agents such as 3-bromopyruvate, 2-bromoacetate, and 2-iodoacetate. As discussed herein, the administration can include a therapeutically effective amount of the anti-cancer composition. In one embodiment, the adverse drug experience can be cachexia. In another embodiment, the adverse drug experience can be pain.

Further, a method for assessing killing efficacy of an anti-cancer composition in a subject can comprise measuring a lactic acid level in the subject prior to administration of the anti-cancer composition; administering the anti-cancer composition to the subject; measuring the lactic acid level in the subject after administration of the anti-cancer composition; and determining the killing efficacy by measuring and/or correlating the difference between the lactic acid levels as a function of treatment time. The anti-cancer composition can be any of those described herein.

The lactic acid levels can be measured from a biological fluid from the subject. In one embodiment, the biological fluid can be selected from the group consisting of: blood and blood fractions, tears, sweat, urine, ascitic fluid, saliva, and combinations thereof. Additionally, the measuring can be colormetric using lactic acid binding enzymes. In one embodiment, the measuring can be by dip-stick or strip methods. In another embodiment, the measuring can be by magnetic resonance imaging.

In certain embodiments, the above-described anti-cancer compositions can comprise one or more of the cellular energy inhibitors, glycolysis inhibitors, mitochondria inhibitors, halo monocarboxylate compounds, and a second chemotherapeutic agent.

The term chemotherapeutic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Further, the following additional drugs may also be used in combination with the antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons α, β, and γ; hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; Lhymosin-α-1; γ-globulin; superoxide dismutase (SOD); complement factors; anti-angiogenesis factors; antigenic materials; and pro-drugs.

Preferred chemotherapeutic agents for use with the compositions and methods of treatment described herein include, but are not limited to altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, etoposide, Floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interferon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

All of the above drugs and additives may be added individually, in combination, as long as there is no negative interaction between or among the various drugs.

Additionally, the present invention provides kits for the treatment of cancer. The present kits provide the necessary ingredients with instructions such that one of ordinary skill in the art can combine the ingredients into an appropriate dosage form for delivery to a subject. At a minimum, a kit would include a cellular energy inhibitor ingredient, at least one sugar ingredient, a glycolysis inhibitor ingredient, a biological buffer ingredient, a container, and a set of instructions. Typically, the ingredients can be admixed such that the dosage form can be administered to a subject for the treatment of cancer. As described herein, such dosage can be part of a regimen for the treatment of various cancers.

In one embodiment, a kit for treatment of cancer can comprise a) a cellular energy inhibitor ingredient having the structure according to formula I (I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl; b) at least one sugar ingredient, which stabilizes the cellular energy inhibitor ingredient by substantially preventing the cellular energy inhibitor ingredient from hydrolyzing; c) a glycolysis inhibitor ingredient; d) a biological buffer ingredient that is present in an amount sufficient to at least partially deacidify the cellular energy inhibitor ingredient and neutralize metabolic by-products of the cellular energy inhibitor ingredient; e) a container for containing the ingredients; and f) a set of instructions for the preparation of a dosage form using the ingredients and for administration of the dosage form to a subject.

In one embodiment, the ingredients can be further contained in individual containers inside the container.

In one embodiment, the kit can further contain a syringe filter for sterilization of at least one ingredient and sterile gloves.

In one embodiment, the kit can contain the cellular energy inhibitor in powdered form in an amount that provides a concentration of about 2.5 mM to about 5.0 mM when added to the solution.

In addition to the above, the ingredients of the kit can be modified as described herein.

Further, the present invention provides a use of a cellular energy inhibitor in the manufacture of an anti-cancer medicament for the treatment of a cancer, wherein the anti-cancer medicament comprises a) a cellular energy inhibitor having the structure according to formula I (I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl;

b) at least one sugar, which stabilizes the cellular energy inhibitor by substantially preventing the inhibitor from hydrolyzing;

c) a glycolysis inhibitor; and d) a biological buffer that is present in an amount sufficient to at least partially deacidify the cellular energy inhibitor and neutralize metabolic by-products of the cellular energy inhibitor.

In one embodiment, the anti-cancer medicament can be suitable for administration to a subject in a therapeutically effective amount.

In one embodiment, the anti-cancer medicament can be administered to a subject when the subject's blood insulin/glucagon ratio is in the range of about 1 to about 10.

In one embodiment, the anti-cancer medicament can be administered to a subject after fasting for at least 4 hours.

In one embodiment, the anti-cancer medicament can be suitable for administration by a method selected from the group consisting of: inter-arterially, intravenously, inter-peritoneally, inhalation, intra-tumorally, orally, topically, and subcutaneously.

In one embodiment, the administration can be inter-arterially.

In one embodiment, the anti-cancer medicament can be suitable for intra-arterially or intravenously administration for a duration from about 30 minutes to about 8 hours.

In one embodiment, the anti-cancer medicament can be suitable for intra-arterially or intravenously administration for a duration from about 3 hours to about 5 hours.

In one embodiment, the administration can include a regimen lasting from about 1 week to 24 weeks.

In one embodiment, the therapeutically effective amount can include a dosage equivalent to about 1 mM to about 10 mM of the anti-cancer composition in a volume of 25 ml to 1000 ml.

In one embodiment, the cancer can be selected from the group consisting of: childhood fibrolamellar hepatocellular carcinoma (FHCC), hepatocellular carcinoma (HCC), non small cell lung cancer, colon cancer, breast cancer, pancreatic cancer, liver cancer, and combinations thereof.

The following examples illustrate a number of embodiments of the present compositions, systems, and methods that are presently known. However, it is to be understood that the following are only exemplary or illustrative of the application of the principles of the present compositions, systems, and methods. Numerous modifications and alternative compositions, methods, and systems may be devised by those skilled in the art without departing from the spirit and scope of the present systems and methods. The appended claims are intended to cover such modifications and arrangements. Thus, while the present compositions, systems, and methods have been described above with particularity, the following examples provide further detail in connection with what are presently deemed to be the acceptable embodiments.

EXAMPLE

Example 1

Rat Hepatocellular Carcinoma Study

Figure 3:
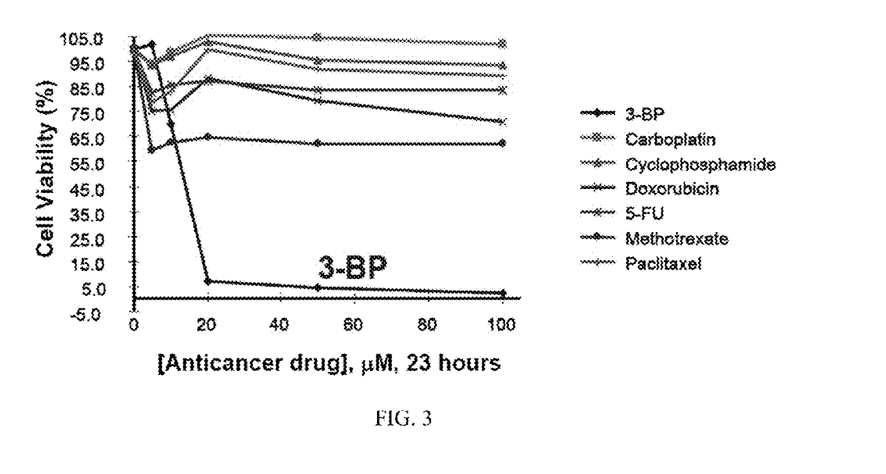
FIG. 3 is a plot of cell viability for hepatocellular carcinoma vs. μM of various anti-cancer agents in accordance with an embodiment of the present invention.

Hepatocellular carcinoma cells were treated with various anti-cancer agents including 3-bromoacetate. FIG. 3 shows a graph of cancer cell viability as a function of μM amounts of the anti-cancer agents over a 23 hour period. As shown in FIG. 3, 3-bromopyruvate provided little cell viability (approx. 5%) with as little as 20 μM used. In fact, 3-bromopyruvate provided 10 times more efficiency as compared to the closest anti-cancer agent, methotrexate, measured in terms of cell viability 5% vs 55%.

Example 2

Lung Cancer Treated with 3-Bromopyruvate

Table 1 provides results of cell proliferation for human lung cancer cells treated with various known anti-cancer agents compared to 3-bromopyruvate.

TABLE 1

| Anticancer Agent at 50 μM, for 24 hrs | Inhibition of Cell Proliferation, % |
|---|---|
| None (control) | 0 |
| 3-Bromopyruvate | 92.5 |
| Carboplatin | 4.5 |
| Cyclophosphamide | 0 |
| Doxorubicin | 39.6 |
| 5-Fluorouracil | 17.8 |
| Methotrexate | 28 |
| Paclitaxel | 0 |

As can be seen from Table 1, for lung cancer cells, 3-bromopyruvate was more than twice as effective as the closest comparative known anti-cancer agent. As such, the present anti-cancer compositions can provide at least a 90% inhibition of cancer cell proliferation.

Example 3

Metastatic Lung Cancer Study

Figure 4A:
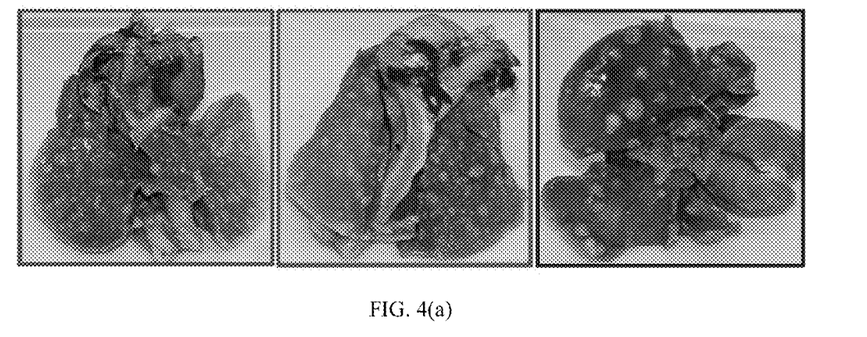
Figure 4B:
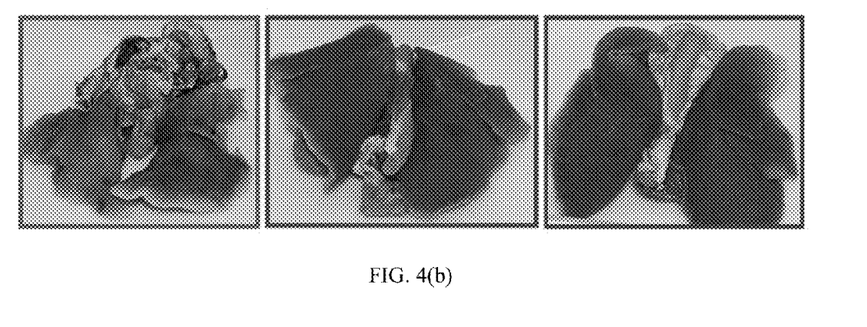

FIG. 4(a) shows pictures of dissected lungs of a rabbits having metastatic tumors without the present treatment, while FIG. 4(b) shows lungs of a rabbits demonstrating no metastatic lung cancer after treatment using 3-bromoacetate via IP port delivery. As can be seen from FIGS. 4(a) and 4(b), the present anti-cancer composition was able to prevent metastatic lung tumors.

While the forgoing description and examples are illustrative of the principles of the present invention in one or more particular applications, it will be apparent to those of ordinary skill in the art that numerous modifications in form, usage and details of implementation can be made without the exercise of inventive faculty, and without departing from the principles

What is claimed is:

1. An anti-cancer composition comprising:
   a) a cellular energy inhibitor having the structure according to formula I wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl;
   b) at least one sugar, which stabilizes the cellular energy inhibitor by substantially inhibiting the inhibitor from hydrolyzing;
   c) a glycolysis inhibitor; and
   d) a biological buffer that is present in an amount sufficient to at least partially deacidify the cellular energy inhibitor and neutralize metabolic by-products of the cellular energy inhibitor
   wherein the anti-cancer composition treats a cancerous tumor that is positron emission tomography (PET) positive.

2. The anti-cancer composition of claim 1, wherein R of formula (I) is OH and X of formula (I) is selected from the group consisting of: a halide, a sulfonate, a carboxylate, an alkoxide, and an amine oxide.

3. The anti-cancer composition of claim 1, wherein the cellular energy inhibitor is a 3-halopyruvate selected from the group consisting of: 3-fluoropyruvate, 3-chloropyruvate, 3-bromopyruvate, 3-iodopyruvate, and combinations thereof.

4. The anti-cancer composition of claim 1, wherein the composition comprises a second sugar and a third sugar independently selected from the group consisting of mannitol, erytritol, isomalt, lactitol, maltitol, sorbitol, xyolitol, dulcitol, ribitol, inositol, and combinations thereof.

5. The anti-cancer composition of claim 4, wherein the sugars are glycerol, inositol, and sorbitol and wherein the composition comprises glycerol in a range from about 0.1 wt % to about 3 wt %, inositol in a range from about 1 wt % to about 5 wt %, and sorbitol in a range from about 30 wt% to about 50 wt %.

6. The anti-cancer composition of claim 1, wherein the glycolysis inhibitor is 2-deoxglucose.

7. The anti-cancer composition of claim 1, wherein the composition comprises the glycolysis inhibitor in a concentration from about 1 mM to about 5 mM.

8. The anti-cancer composition of claim 1, wherein the biological buffer is selected from the group consisting of a citrate buffer, a phosphate buffer, and an acetate buffer.

9. The anti-cancer composition of claim 1, wherein the biological buffer is a citrate buffer.

10. The anti-cancer composition of claim 1, wherein the by-product is a hydrogen halide and the biological buffer is sodium citrate.

11. The anti-cancer composition of claim 1, wherein the composition comprises the biological buffer in a concentration from about 1 mM to about 20 mM and maintains a physiological pH of 5.5 to 8.0.

12. The anti-cancer composition of claim 1, further comprising a halo monocarboxylate compound.

13. The anti-cancer composition of claim 12, wherein the halo monocarboxylate compound is 2-bromoacetate.

14. The anti-cancer composition of claim 12, wherein the composition comprises the halo monocarboxylate compound in a concentration from about 0.1 mM to about 0.5 mM.

15. The anti-cancer composition of claim 1, further comprising a mitochondrial inhibitor.

16. The anti-cancer composition of claim 15, wherein the mitochondrial inhibitor is selected from the group consisting of: oligomycin, efrapeptin, aurovertin, and mixtures thereof.

17. The anti-cancer composition of claim 15, wherein the composition comprises the mitochondrial inhibitor in a concentration from about 0.01 mM to about 0.5 mM.

18. A method for the treatment of cancer, comprising administering to a subject the anti-cancer composition of claim 1 in a therapeutically effective amount.

19. A method of minimizing toxicity of a cellular energy inhibitor of formula (I) to a subject receiving the cellular energy inhibitor comprising, combining in the subject, the cellular energy inhibitor with a biological buffer that is present in an amount sufficient to at least partially deacidify the cellular energy inhibitor and neutralize metabolic by-products of the cellular energy inhibitor due to its chemical reaction and/or cellular metabolism:

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl.

20. A method of minimizing an adverse drug experience associated with administration of an anti-cancer composition to a subject, comprising administering the anti-cancer composition to the subject at a time when the subject's blood insulin/glucagon ratio in the range of about 1 to about 10; the anti-cancer composition comprising the inhibitor of formula (I):

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl, wherein the anti-cancer composition treats cancerous tumors that are positron emission tomography (PET) positive.

21. A method for assessing killing efficacy of an anti-cancer composition in a subject, comprising
a) measuring a lactic acid level in the subject prior to administration of the anti-cancer composition;
b) administering the anti-cancer composition to the subject;
c) measuring the lactic acid level in the subject after administration of the anti-cancer composition; and
d) determining the killing efficacy by measuring and/or correlating the difference between the lactic acid levels as a function of treatment time;
wherein the anti-cancer composition comprises
i) a cellular energy inhibitor having the structure according to formula I (I)

wherein X is selected from the group consisting of: a nitro, an imidazole, a halide, sulfonate, a carboxylate, an alkoxide, and amine oxide; and R is selected from the group consisting of: OR', N(R'')$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R'' represents H, C1-C6 alkyl, or C6-C12 aryl, and R''' represents H, C1-C20 alkyl or C6-C12 aryl;
ii) at least one sugar, which stabilizes the cellular energy inhibitor by substantially inhibiting the inhibitor from hydrolyzing;
iii) a glycolysis inhibitor; and
iv) a biological buffer that is present in an amount sufficient to at least partially deacidify the cellular energy inhibitor and neutralize metabolic by-products of the cellular energy inhibitor,
wherein the anti-cancer composition treats cancerous tumors that are positron emission tomography (PET) positive.

22. The anti-cancer composition of claim 1, wherein the cancerous tumor is in a tissue selected from the group consisting of brain, colon, urogenital, lung, renal, prostate, pancreas, liver, esophagus, stomach, hematopoietic, breast, thymus, testis, ovarian, skin, bone marrow, and uterine.

23. The method of claim 20, wherein the cancerous tumor is in a tissue selected from the group consisting of brain, colon, urogenital, lung, renal, prostate, pancreas, liver, esophagus, stomach, hematopoietic, breast, thymus, testis, ovarian, skin, bone marrow, and uterine.

24. The method of claim 21, wherein the cancerous tumor is in a tissue selected from the group consisting of brain, colon, urogenital, lung, renal, prostate, pancreas, liver, esophagus, stomach, hematopoietic, breast, thymus, testis, ovarian, skin, bone marrow, and uterine.

25. The method of claim 19, wherein the cellular energy inhibitor is 3- bromopyruvate.

26. The method of claim 19, wherein the biological buffer is selected from the group consisting of a citrate buffer, a phosphate buffer, and an acetate buffer.

27. The method of claim 19, wherein the biological buffer is a citrate buffer.

28. The method of claim 19, wherein the biological buffer maintains a physiological pH of 4.0 to 8.5 in the subject.

29. The method of claim 19, wherein the biological buffer maintains a physiological pH of 5.5 to 8.0.

30. The method of claim 19, wherein the cellular energy inhibitor and biological buffer are present in a ratio ranging from 1:1 to 1:5 by mM.

31. The method of claim 20, wherein the insulin/glucagon ratio is in the range of about 2 to about 5.

32. The method of claim 20, wherein the anti-cancer composition is administered to the subject after fasting for at least 4 hours.

33. The method of claim 20, wherein the administration is selected from the group consisting of: inter-arterially, intravenously, inter-peritoneally, inhalation, intra-tumorally, orally, topically, and subcutaneously.

34. The method of claim 33, wherein the administration is inter-arterially.

35. The method of claim 20, wherein the anti-cancer composition is intra-arterially or intravenously administered for a duration from about 30 minutes to about 8 hours.

36. The method of claim 20, wherein the anti-cancer composition is intra-arterially or intravenously administered for a duration from about 3 hours to about 5 hours.

37. The method of claim 20, wherein the administration includes a regimen lasting from about 1 week to 24 weeks.

38. The method of claim 20, wherein the administration includes a therapeutically effective amount of the anti-cancer composition.

39. The method of claim 38, wherein the therapeutically effective amount includes a dosage of about 1 mM to about 10 mM of the anti-cancer composition in a volume of 25 ml to 1000 ml.

40. The method of claim 20, wherein the adverse drug experience is cachexia.

41. The method of claim 20, wherein the adverse drug experience is pain.

42. The method of claim 21, wherein the lactic acid levels are measured from a biological fluid from the subject.

43. The method of claim 42, wherein the biological fluid is selected from the group consisting of: blood and blood fractions, tears, sweat, urine, ascitic fluid, saliva, and combinations thereof.

44. The method of claim 21, wherein measuring is by colormetry using lactic acid binding enzymes.

45. The method of claim 21, wherein the measuring is by dip-stick or strip methods.

46. The method of claim 21, wherein the measuring is by magnetic resonance imaging.

* * * * *